United States Patent [19]

Pierce et al.

[11] Patent Number: 5,236,845
[45] Date of Patent: Aug. 17, 1993

[54] ON-LINE IRON (II) CONCENTRATION MONITORING TO CONTINUOUSLY DETERMINE CORROSION IN BOILER SYSTEMS

[75] Inventors: Claudia C. Pierce, Lisle; Roger W. Fowee, Wheaton; Rodney H. Banks, Naperville, all of Ill.

[73] Assignee: Nalco Chemical Company, Naperville, Ill.

[21] Appl. No.: 965,130

[22] Filed: Oct. 22, 1992

[51] Int. Cl.⁵ .............................................. G01N 31/22
[52] U.S. Cl. ...................................... 436/6; 436/84; 436/166
[58] Field of Search .................... 436/6, 84, 166, 164; 73/86, 61.41

[56] References Cited

U.S. PATENT DOCUMENTS

| | | | |
|---|---|---|---|
| Re. 30,983 | 6/1982 | Stookey | 436/84 |
| 3,709,662 | 1/1973 | Hach | 436/84 |
| 3,770,735 | 11/1973 | Stookey | 544/182 |
| 3,836,331 | 9/1974 | Stookey | 436/84 |

OTHER PUBLICATIONS

Jacklin, C. et al. "Dissolved Hydrogen Analyzer-a Tool for Boiler Corrosion Studies" Materials Protection and Performance, May 1971.

Uhlig et al. "An Introduction to Corrosion Science and Engineering" Corrosion and Corrosion Control, 3rd edition, John Wiley & Sons (1985).

Clark, "Iron (II) Determination in the Presence of Iron (III) Using 4,7-diphenyl-1,10-phenanthrolene" Analytical Chemistry, vol. 34, pp. 348-352 (1962).

Alonzo, J. et al. "Sandwich Techniques in Flow Injection Analysis, Part Two, Simultaneous Determination of Iron (II) and Total Iron" Analytica Chemica Acta, vol. 219, pp. 345-350 (1989).

Artis, J. et al. "Study of Continuous Flow Automation for Serum Iron on Comparing Several Sensitive Reagents" Micro Chemical Journal, vol. 28, pp. 275-284 (1983).

Shi-yu et al. "Micro Determination of Iron in Water by Ion Exchanger Colorimetry with Ferrozine" Talanta, vol. 31 p. 844 (1984).

Bornack, W. E. "The Chemistry of Iron and Its Corrosion Products in Boiler Systems" National Association of Corrosion Engineers, Corrosion Magazine, pp. 154-158 (1987).

Mayor, P. et al. "Application of Dissolved Hydrogen Measurement Technique for Monitoring of Corrosion in High Pressure Boilers" International Corrosion Forum, Corrosion, Paper No. 57 (1984).

Bain et al. "Hydrogen Monitoring as a Method for Monitoring Corrosion in Steam Generating Systems" Corrosion, Paper no. 184 (1990).

Gibbs, C. R. et al. "Characterization in.Application of Ferrozine Iron Reagent as Ferrous Iron Indicator" Analytical Chemistry, vol. 48, pp. 1197-1201 (1976).

Stookey, L. L. "Ferrozine-A New Spectrophotometric Reagent for Iron" Analytical Chemistry, vol. 42, No. 7, pp. 779-781 (1970).

Fadras, H. et al. "Suppression of Iron (III) Interference in the Determination of Iron (II) in Water by the 1,10-Phenanthrolene Method" Analyst, vol. 100, pp. 549-553 (1975).

Joneson, D. H. "Hydrogen Analysis as Method of Corrosion Monitoring in Biolers" Combustion, pp. 14-17 (1979).

(List continued on next page.)

*Primary Examiner*—James C. Housel
*Assistant Examiner*—Jeffrey R. Snay
*Attorney, Agent, or Firm*—Robert A. Miller; James J. Drake

[57] ABSTRACT

A method for determining the presence of ferrous ion in boiler waters is described. The method can be used to directly measure the rate of corrosion occurring in boiler waters, and can measure the corrosion rates in the presence of boiler water treatment chemicals. The method uses a complex formed between only ferrous ion and a chemical 3-(2-pyridyl)-5,6-diphenyl-1,2,4-triazine-p,p'-disulfonic acid monohydrate reagent.

9 Claims, 5 Drawing Sheets

OTHER PUBLICATIONS

"The Kinetics of the Schikoor Reaction on Steel Surfaces at Low Temperature" NACE Corrosion, Paper No. 311 (1989).

Bohnsack, G. "Towards an Understanding of the Schikoor Reaction" VGB Mitteilunge, pp. 1–39 (1971).

Bohnsack, G. "The Solubility of Magnetite in Water and in Aqueous Solutions of Acidi and Alkali" Vulkan-Verlag Essen (1987).

Noack, M. G. "Oxygen Scavengers" NACE Corrosion, Paper No. 436 (1989).

Montgomery, J. M. "Water Treatment Principles and Design" John Wiley & Sons, New York, pp. 392–434 (1985).

Oriani, R. A. et al. "Hydrogen Degradation of Ferrous Alloys" Noves Publishing, p. 251 (1985).

Sweeton, F. H. et al. "The Solubility of Magnetite and Hydrolysis of Ferrous Ion etc." Journal of Chemical Thermodynamics, vol. 2, p. 479 (1970).

Sandell, E. B. "Photometric Determination of Traces of Metals" Interscience, New York, pp. 362–371 (1957).

Bases, C. F. et al. "The Hydrolysis of Cations" John Wiley & Sons, New York, p. 236 (1976).

"Keys to Chelation" Dow Chemical Company, Midland, Mich., pp. 4:14–22 (1980).

"Consensus on Operating Practices for the Control of Feedwater and Boiler Water Quality in Modern Industrial Boilers" ASME, N.Y. (1979).

"the Merck Index" 10th ed., Merck & Co., Inc., p. 1337 (1983).

Uhlig, H. H. "Corrosion and Corrosion Control" John Wiley & Sons, New York, pp. 79–80 and 246–249 (1963).

Evans, U. R. "The Corrosion and Oxidation of Metals: Scientific Principles and Practical Applications" London, Edward Arnold Ltd., 1960, pp. 184–185 and 999–1000.

ON-LINE IRON (II) CONCENTRATION MONITORING TO CONTINUOUSLY DETERMINE CORROSION IN BOILER SYSTEMS

BACKGROUND OF THE INVENTION

1. Field of the Invention

The invention relates to a method for detecting corrosion and ferrometals, and, more particularly, to corrosion of ferrometals in boiler system units.

2. Description of the Prior Art

Potential corrosion problems in boiler systems have presented boiler operators with many unanswered questions over the history of operating these boiler systems. Problems have increased as the boiler systems themselves have become more sophisticated. Boiler systems that operate at extremely high pressures and temperatures require pretreatment of waters being used to feed the boilers to eliminate contaminants, such as calcium and magnesium, inorganic salts such as ferrous and ferric salts, silicates and the like.

Corrosion reactions in all boiler systems have been demonstrated by many previous researchers to be affected by many parameters, such as oxygen content, water pH, temperature, pressure, water flow velocity, the formation of certain types of salts and scales, for example hardness scales, iron scales, particularly magnetite, and treatment with boiler water treatment chemicals. The boiler water treatment chemicals are designed to protect the boiler from corrosion, hardness scale deposits, oxygen-induced corrosion, pH excursions, and the like.

Recently, it has been determined that the ferrometals making up boiler system units, which ferrometals can include a number of different types of iron-containing steels, iron alloys, and the like, are faced with particularly difficult corrosion detection problems as far as determining when these boiler system units are experiencing corrosion and determining the reasons why the corrosion is occurring.

The chemistry of iron and its corrosion products in boiler systems has been summarized by W. E. Bornak in an article published in *Corrosion (NACE)*, Volume 44, No. 3, March 1988. Bornak describes the measurement of different types of corrosion of ferrometals in boiler water systems, particularly reviewing investigations of magnetite formation and corrosion related thereto in boilers. Bornak's article primarily summarizes the difficulties caused by corrosion and presents several mechanisms to explain why corrosion is occurring. For example, Bornak speaks of the formation of magnetite through the mechanism of oxygen corrosion and magnetite's protective characteristics when formed on a ferrometal surface in contact with boiler waters, as well as the breakdown of the magnetite layer under certain circumstances.

Bornak broadly describes the difficulties encountered by the production of hydrogen, which is a byproduct of corrosion and which has been traditionally used to measure corrosion rates occurring in an operating boiler. According to Bornak, hydrogen atoms produced through corrosion or through some other side mechanism, can diffuse into the metal and be lost either by direct diffusion or by reactions with various forms of metal oxides encountered by the hydrogen. Hydrogen lost in any of these ways is therefore not available for measurement and the detection of actual corrosion based on hydrogen in an operating boiler is therefore limited.

In the text published by Wiley Interscience Publications, John Wiley and Sons, entitled *Corrosion and Corrosion Control, An Introduction To Corrosion Science and Engineering*, Third Edition, edited by H. H. Uhlig and R. W. Revie, the basic electrochemical theory of corrosion is described in general for iron and steel corrosion in the presence of aqueous media. In anaerobic solutions, the cathodic reaction is presented as the primary reaction responsible for the formation of hydrogen. Since well-operated boilers are operated in essentially oxygen-free environments, thereby qualifying as anaerobic solutions, the cathodic reaction is the primary reaction that produces hydrogen. However, because of the difficulties mentioned above in using hydrogen as a measurement of corrosion, particularly in an operating boiler in the field, other techniques for accurately measuring real time corrosion phenomena are required.

In an article entitled "Dissolved Hydrogen Analyzer—A Tool for Boiler Corrosion Studies", by Jacklin and Wiltsey, published in *Materials Protection and Performance*, May 1971, the authors explain their attempts to provide for a dissolved hydrogen analyzer which is essentially the best method of analysis existing today for monitoring corrosion in an operating boiler system. However, because of the difficulties mentioned above, dissolved hydrogen is not a preferred method.

Another article entitled "Hydrogen Analysis as a Method of Corrosion Monitoring in Boilers", by Joneson, published in *Combustion*, August 1979, points out some of the difficulty in interpreting dissolved hydrogen data and distinguishing from hydrogen formed by generalized and localized corrosion reactions and hydrogen which might be generated from chemical decompositions of boiler water treatment chemicals or from some unknown interference.

In *Corrosion*, April 1984, Paper No. 57 entitled "Application of Dissolved Hydrogen Measurement Technique for Monitoring of Corrosion at High Pressure Boilers", by Mayer, et. al., the authors state that detection and recognition of conditions leading to accelerated corrosion are essential in reducing short and long term metal loss. The authors emphasize hydrogen measurements should be used frequently, but state that the results of the hydrogen measurements would be no more than a summary indication of many processes which may take place within the system. The authors suggest combining hydrogen tests with other analytical and operational parameters. However, these techniques primarily monitor hydrogen values as well as monitoring operational controls in an operating boiler.

In *Corrosion*, 1990, Paper No. 184 presented Apr. 23-27, 1990 by Bane, et. al., the authors discuss internal boiler corrosion leading to the formation of magnetite and hydrogen. The paper again emphasizes hydrogen studies that can be useful in determining corrosion in boilers. As a result, even in 1990, hydrogen analysis was being presented as the primary way of determining boiler corrosion. However, as stated above, hydrogen evolution as a means of measuring corrosion suffers from the difficulties cited above, i.e., hydrogen atom reactions with iron oxides, hydrogen gas diffusion into metal substrates and problems of determining the source of the hydrogen measured as being from corrosion, breakdown of chemical additives, or similar sources.

Each of the articles cited above are incorporated herein by reference.

In an attempt to determine what other techniques might be available to measure iron in boiler waters, the following articles and/or patents have come to Applicants' attention.

An article in *Analytical Chemistry*, Volume 34 (3) March 1962, pages 348-352, teaches the use of 4,7-diphenyl-1,10-phenanthroline for the purpose of determining ferrous ion in the presence of ferric ion. This phenanthroline reagent apparently specifically forms complexes with ferrous ion which complexes have a different absorption spectra than the complexes formed by ferric ion. Although iron corrosion is mentioned in general, there is no mention of boiler waters in the reference.

In *Analyst*, August, 1975 (Volume 100), pages 549-554, Fadrus, et al, teaches a method for determining ferrous ion in water in the presence of ferric ion using 1,10-phenanthroline. Fadrus teaches that ferric ion complexation does provide interferences. The author masks this interference with what is termed "complexones". His recommended complexone is nitrilotriacetic acid (hereinafter NTA). Again, Fadrus, et. al., are concerned primarily with the analytical chemistry of ferrous and ferric phenanthroline complexes and do not disclose or teach the use of this chemistry in boiler waters.

In U.S. Pat. No. 3,836,331, issued to Stookey, the use of 3-(2-pyridyl)-5-6-bis(4-phenylsulfonic acid)-1,2,4-triazine and certain salts thereof, particularly the sodium salts, as useful reagents for spectrophotometric determinations of iron in water and in other solutions is taught. Stookey, column 1, does speak of the necessity to analyze for iron content in boiler waters because the iron oxide content of the water is an index of the rate of corrosion taking place in the boiler. However, it is then taught that conventional methods for analysis of iron normally involve the collection of iron compounds, solubilizing these compounds by adding, e.g., hydrochloric acid, allowing sufficient time for dissolution, and then adding a reducing agent, such as hydroxylamine or hydroxylamine hydrochloride to reduce the iron to the ferrous form. He then specifies the use of 3-(2-pyridyl)-5,6-diphenyl-1,2,4-triazine-p,p'-disulfonic acid, (hereinafter FZ), as a specific complexing agent for ferrous ion. FZ acts as a complexing agent for ferrous ion, ferric ion, cobalt salts, copper salts and the like. It is further taught that FZ acts as a ferrous ion chromogen. Stookey also discloses procedures for monitoring total iron content. The procedures involve collecting samples, dissolving samples, reducing samples specifically by the addition of reducing agents, such as hydroxyl ammonium chloride, adding reagents suitably buffered and measuring iron content by colorimetric means.

U.S. Pat. No. 3,770,735, issued to Stookey, describes FZ compounds but primarily emphasizes the synthesis of these compounds. No mention of actual use in boiler waters is made except by hypothesis that boiler water iron content may be an example where such an analysis might be necessary.

In *Talanta*, Volume 31, No. 10A, pages 844-845, 1984, Li Shi-Yu, et. al, describe the use of ion exchange colorimetry to determine microamounts of iron in water with FZ.

In *Analytical Chemistry*, Volume 42 (7) June 1970, the advantages of using FZ in combination with a digestion procedure for the determination of total iron in various waters is taught. No mention of boilers is made.

Finally, an article appearing in *Analytical Chemistry*, Volume 48(8) July 1976, pages 1197-1201, provides for the characterization and application of FZ as a ferrous ion indicator. A number of references are given showing the use of an FZ reagent and the combination of the reagent in a number of automated analyzers and in a test kit for determination of ferrous ion, primarily in blood serum. In a list of cited references the use of FZ in potable water, sea water, plant solutions, plant materials, high purity reagent chemicals, bathocuproine sulfonate analysis, as well as to determine cobalt, ruthenium, osmium and other metal contents are listed. These various analytical uses take advantage of the fact that the ferrous ion/FZ complex is colored and the ferric ion/FZ complex is not colored. Using this characteristic, FZ has also been used to indirectly detect the presence of ascorbic acid in fruit juices, blood serum and urine, to detect the presence of sulfur dioxide in various liquid samples and after absorption from various gases and various enzymatic activities in the NADH/NAD redox systems. No use in boilers is summarized therein.

SUMMARY OF THE INVENTION

It is an object of our invention to provide for a method of determining the corrosion of ferrometals in boiler system waters.

It is another object of the invention to determine actual corrosion rates of ferrometals, i.e., carbon steels, stainless steels, iron, or other iron alloys, in contact with boiler system waters containing water treatment chemicals. Such chemicals include, but are not necessarily limited to, oxygen scavengers, such as bisulfite, hydrazine, carbohydrazide, erythorbic salts, and the like and other chemical treatments, such as hardness transporting chemicals and certain polymeric complexes, as well as other boiler water treatment chemicals, such as precipitating treatments for hardness, that is phosphates, phosphonates and the like.

It is a further object of the invention to determine actual corrosion rates in various boiler system units containing ferrometals in contact with boiler waters, either containing boiler water treatment chemicals or not containing boiler water treatment chemicals, such as in condensate systems, by obtaining a known aliquot volume of a boiler water sample in an anaerobic environment, then adding the aliquot sample to a solution of FZ to form a soluble complex with FZ or its salts. After formation of the ferrous ion/FZ complex, the complex is relatively stable to oxidation. The presence of the complex is measured spectrophotometrically by measuring within a reasonable time period of from about 1 minute to about 48 hours. The absorbance of a known standard containing this complex is compared with a concentration of an unknown sample having known aliquot relationships at a wave length of about $560 \pm 30$ nanometers.

Finally, the amount of ferrous ion present in the boiler waters is calculated by making a comparison of absorbance between the aliquot sample and known samples and to continuously measure this concentration by repeating in a manner to provide for the measurement of actual corrosion rates of ferrometals in contact with boiler system waters.

DETAILED DESCRIPTION OF THE PREFERRED EMBODIMENT

Applicants' invention comprises a method of determining actual corrosion rates of ferrometals in contact with boiler system waters containing or not containing boiler water treatment chemicals. Applicants' method is a step-wise process as follows:

Step 1: Obtain a known aliquot volume of a boiler water sample from a boiler system unit in an anaerobic environment.

Step 2: Add the known aliquot volume of the sample to a known volume of an acetate buffered standardized solution of 3-(2-pyridyl)-5,6-diphenyl-1,2,4-triazine-p,p'-disulfonic acid monohydrate, or salts thereof, and mix to obtain a solution of a water soluble ferrous ion/FZ complex.

Step 3: Place the solution of the soluble ferrous ion/FZ complex into a photometric cell of prescribed length and spectrophotometrically measure the absorbance of said ferrous ion/FZ complex at a wave length of about $560 \pm 30$ nanometers.

Step 4: Calculate the amount of ferrous ion present in said solution of ferrous ion/FZ complex by comparing the absorbance obtained in Step 3 with the absorbance measured by generating a standard ferrous ion/FZ absorbance curve. The curve is generated using known concentrations of ferrous ion from 1 to about 1000 parts per billion.

Step 5: Repeat steps 1–4, as necessary, to determine actual corrosion rates over a known time period.

The FZ reagent is primarily the monosodium salt of FZ having one water of hydration related thereto and can be commercially purchased from the Hach Company. Other salt forms of FZ may also be used in Applicants' process. The complexing agent should be used at a known pH of from about 2.0 to about 6.0, preferably from between about 3.0 and about 5.0 and most preferably at a pH of approximately $3.6 \pm 0.2$. The standardized solution of the FZ reagent primarily is a solution of the FZ complexing agent that preferably contains an acetate buffer such that the pH ranges between $3.6 \pm 0.2$, although other buffering systems besides the acetate buffering system may be used.

As stated above, it is critical to maintain an anaerobic environment. This is because the initial reactions involving corrosion of ferrometals in contact with boiler waters create ferrous ions. Subsequent reactions of ferrous ion with oxygen or other chemicals provide for quite complicated forms of other iron salts some or all of which are insoluble in water and either form as scales or as precipitates in the boiler water. Therefore, the initial samples taken from each boiler system unit must be taken in a manner which preserves the anaerobic environment. It will be understood that these are the only measures used to protect the system from oxygen or from oxidizing species. That is to say, no reducing agents or other oxygen scavengers are added to the sample after it is removed from the system.

The known aliquot volume of the sample is immediately added to a known volume of the FZ reagent solution, buffered as above. Although an acetate buffer is used primarily in our technique, any other buffer in the pH range between about 2.0 and 6.0 would be sufficient. Buffering ingredients which might form precipitates with boiler chemicals or contaminants should be avoided. It is preferable that the complex solutions formed be maintained in an anaerobic environment, although these complexes are considerably more stable against oxygenation than are the original solutions. It is advisable to maintain some protection against exposure to air or oxygen during the entire process of Applicants' invention.

The reaction between ferrous ions in the boiler water samples as taken and described above and the FZ reagent solution is nearly instantaneous. However, it is advisable to provide some mixing and some reaction time to assure that a homogeneous solution of the water soluble ferrous ion/FZ complex has been obtained prior to measurement of its concentration spectrophotometrically.

The spectrophotometric measurement can use any equipment available which has the capability of presenting a light source having a wave length of about $560 \pm 30$ nanometers through a controlled cell length path into which the ferrous ion/FZ complex solution has been added, and which equipment includes means for measuring light absorbance, light transmission and the like, through the spectrophotometric cell containing the ferrous ion/FZ complex solution.

Figure 1:
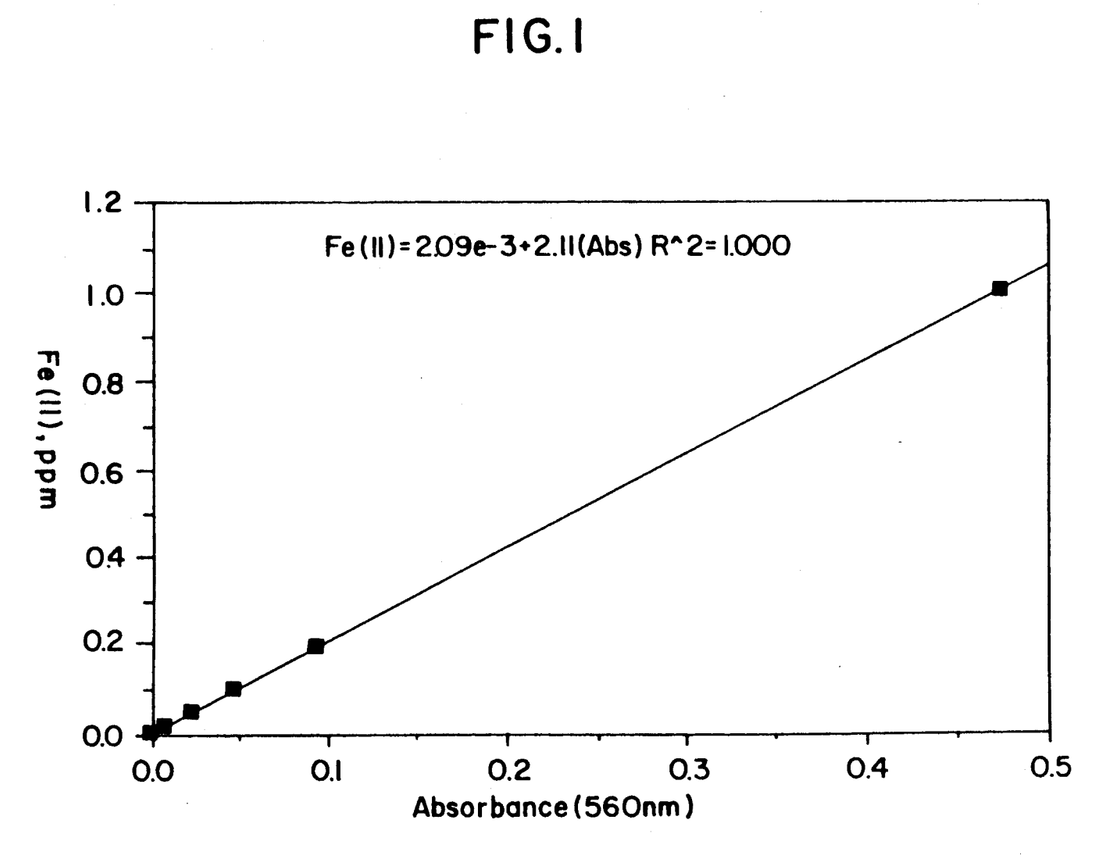
FIG. 1 is a standard absorbance curve describing the absorbance of a ferrous ion/FZ complex at 560 nanometers.

After measuring absorbance of the ferrous ions/FZ complex at the above wave length the amount of ferrous ion present in the boiler water sample is calculated by comparing the absorbance of the ferrous ion/FZ complex with a standard absorbance curve. Such a standard curve is presented as FIG. 1 and describes the absorbance at 560 nanometers of a ferrous ion/FZ complex as measured according to the techniques of Applicants' invention.

To measure the corrosion rates of boiler system ferrometals in contact with boiler waters, particularly those boiler waters containing treatment chemicals, it is advisable that the iron/FZ complex be present in the standardized solution to which the boiler water sample is added in sufficient concentration to overwhelm any additional complexes or reactions that might be occurring or which might have already occurred between ferrous ion as generated by the corrosion reactions, and whatever treatment chemicals are present. For example, it is known that ethylene diamine tetraacetic acid, hereinafter EDTA, a known boiler water treatment chemical, can form complexes with ferrous ion. It has been shown that these complexes can interfere with the reaction of ferrous ion with the FZ reagent. However, by increasing the concentration of the FZ reagent the interference is overwhelmed and the equilibrium for forming the ferrous ion/EDTA complex is no longer controlling. Since boiler waters may be treated with EDTA, and such other complexing reagents as nitrilotriacetic acid, (hereinafter NTA), for the purpose of controlling hardness formation and hardness scales, it is unlikely that EDTA or NTA or like complexing agents are going to be present in the boiler waters sampled in concentrations much above from about 0.5 to about 50 parts per million, even though those boiler waters are being treated specifically by formulations containing these strong complexing agents. As a result, it has been found that the reagent containing the FZ complexing agents should provide for essentially quantitative formation of ferrous ion/FZ complexes in the presence of concentrations of the FZ complexing agent ranging from approximately 0.005 to about 0.20 molar concentration of FZ complexing agent in the acetate buffer solution. A preferred concentration of the FZ complexing agent in this buffered solution, in the absence of EDTA/NTA, or like chemical complexing agents, is at about 0.025 molar, although higher concentrations are permitted. (See Table II).

TABLE II

Required concentration of ferrozine reagent to compensate for EDTA interference (Fe(II) = 300 ppb)

| EDTA Concentration (as $CaCO_3$) | Ferrozine [M] |
|---|---|
| 0 | 0.025 |
| 2 | 0.071 |
| 20 | 0.141 |

The boiler system can contain a number of different boiler system units, each unit subject to corrosion according to the reactions cited in the references incorporated herein by reference and presented above. The primary reaction for corrosion is the reaction of iron metal with water to form ferrous ion, and a similar reaction of the protons in water to form hydrogen gas, the reactions occurring at the anodic and/or cathodic sites respectively. If samples are taken of the boiler waters immediately within the boiler water system being monitored, are maintained in an anaerobic environment and are added immediately to the FZ reagent solutions as described above, the complex formed is sufficiently stable to permit its spectrophotometric measurement. Therefore, the direct measurement of instantaneous corrosion occurring within the boiler system or the boiler system unit being monitored is now available, with no drawbacks as in hydrogen measurement.

These boiler system units can include, but are not necessarily limited to, the inlet and/or outlet of an economizer, the inlet and/or outlet of the pre-heaters, the inlet and/or outlet of each steam condensors, the actual feed water to the boiler, the actual blow down from the boiler, the inlet and/or outlet samples obtained from any storage vessel or any holding tank or any aqueous condensate receiver, any steam receiver which is undergoing condensation to provide a liquid sample therein, any heat exchanger, any working unit being driven by the steam generation such as a turbine, a piston and the like. Also, samples from the water wall header and outlet of the deaerator, inlet and outlet of the water treatment system providing for low hardness water, such treatment facilities including ion exchange and the like may be monitored for corrosion. Also, water samples in any line, any pump, any vessel, and the like, which devices are contained in a boiler system may be so monitored.

Although total iron analysis has been run and hydrogen analysis has been run in an attempt to detect direct corrosion, these procedures have fallen by the wayside either because of complications in measuring corrosion rates in the field or because of the unsureness that the corrosion rates that were measured depended in fact upon the chemicals species being measured. By direct measurement of ferrous ion in boiler water samples which samples are being collected directly from boiler water units within an operating boiler, this unsureness is eliminated.

To provide for better understanding of our invention, the following examples are given.

EXAMPLES

A. Into a one liter volumetric flask, 72.12 grams of sodium acetate, as the trihydrates, and 274.29 milliliters of glacial acetic acid were added with sufficient distilled water to bring to volume. The resulting solution is buffered at a pH of 3.6±0.2.

B. 50 milliliters of the above buffer solution was added to a 100 milliliter volumetric flask to which was added 1.28 grams of FerroZine ®[1] reagent. Ferrozine ® is an analytical quantitative reagent obtained from the Hach Chemical Company, Ames, Iowa. The FerroZine ® reagent is the monosodium salts, as a monohydrate, of 3-(2-pyridyl)-5,6-bid(4-phenylsulfonic)-1,2,4-triazine.

[1] FerroZine ® is a registered trademark of Hach Chemical Company.

The flask is then brought to volume with the buffer solution. The FZ/reagent solution contains 0.025 molar concentration of the FZ complexing agent and is buffered at a pH of 3.6±0.2.

C. A 100 part per million standard solution of ferric ion was prepared by adding 0.860 grams of ferric ammonium sulfate, 12 hydrates, to a small beaker to which was also added 4 milliliters of analytically pure nitric acid and approximately 50 milliliters of distilled water. The solution was heated to a gentle boil until all of the solids had dissolved. The solution was cooled and another 6 milliliters of ultrapure nitric acid was added. The contents of the beaker were analytically transferred to a one liter volumetric flask and made up to volume with distilled water. The solution so prepared has a ferric ion concentration of 100 parts per million.

D. A standard solution containing 100 parts per million ferrous ion was made up by adding 0.701 grams of ferrous ammonium sulfate, 6 hydrates, to a 1 liter volumetric flask and adding sufficient distilled water to bring to volume. The resulting solution has a ferrous ion concentration of 100 parts per million. The solution is protected from oxygen or oxidizing chemicals and is used as soon as it is prepared.

Using the ferric ion solution and the ferrous ion solution, a standard absorbance-concentration curve was generated for the determination of the percent of ferrous ion in solution. A series of 50 milliliter volumetric test tubes had 1 milliliter of the FZ reagent added to each. A blank solution was prepared by diluting with distilled water to the 50 milliliter mark and various standard concentrations of ferrous ion were made by adding different concentrations of the ferrous ion standard solution to these test tubes and bringing to volume with the standard FZ reagent solution. Color development of the ferrous ion/FZ complex occurred over a period of about 1-10 minutes and the absorbance of each of the solutions contained in a photometric cell of known rate was measured at a wavelength of 560 nanometers. The standard absorbance curve is presented in FIG. 1. This standard absorbance curve is essentially unchanged, even in the presence of ferric ion, since the ferric ion-FZ complex does not absorb light of this general 560±30 nanometer wavelength. (See the results in Table I)

Samples of boiler waters were obtained from various operating boiler system units by taking the water sample in a manner that guaranteed the sample was maintained in an anaerobic environment. Samples were taken in such a manner so as to provide a known volume of the boiler water samples and the sample was added immediately to the standard solution of FZ reagent as prepared above. This was also done in a manner to maintain both the FZ solution and the boiler samples in an anaerobic environment.

compensate for any interferences caused by the boiler water treatment chemicals.

Figure 4:
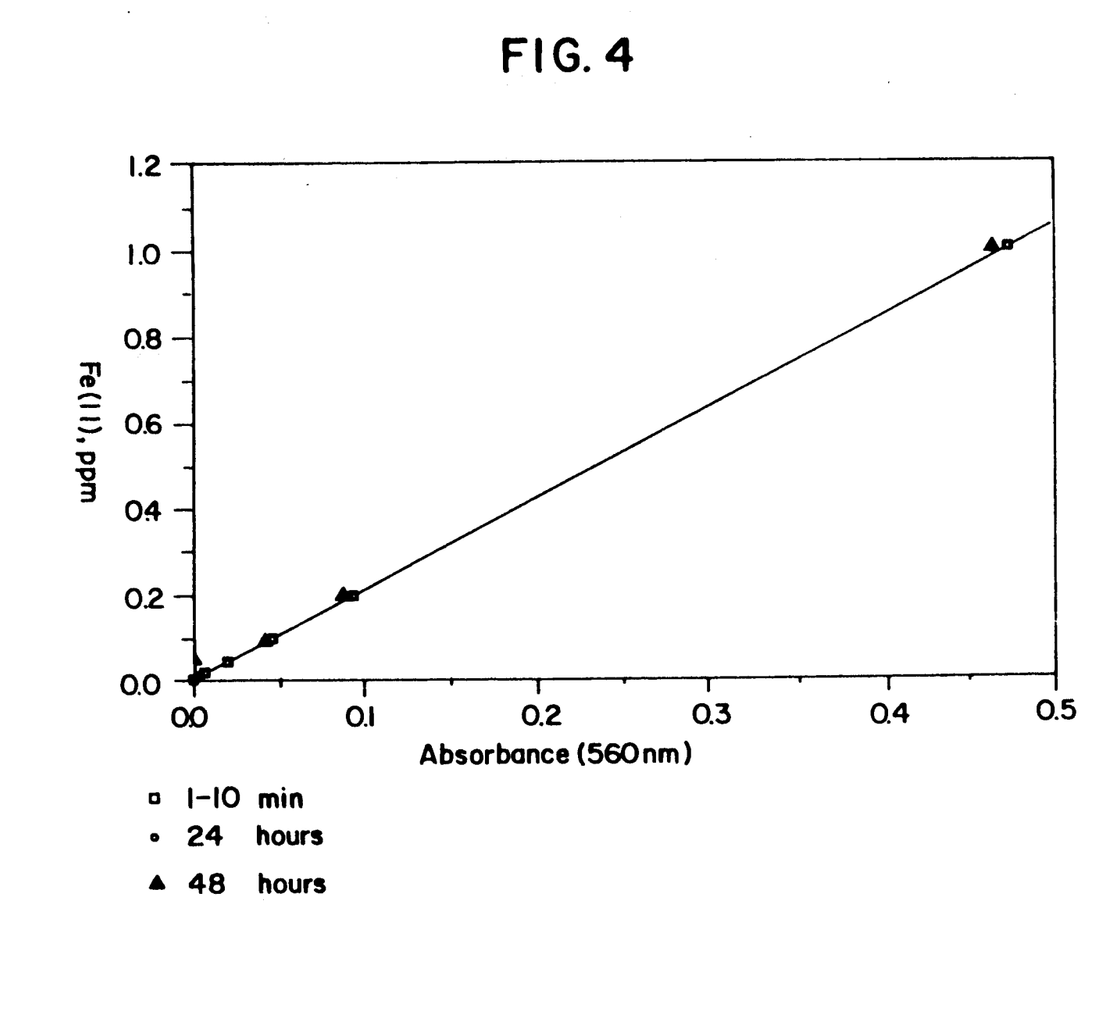
FIG. 4 is a graph showing the absorbance of ferrous ion/FZ complex as a function of time.

The time required for development of the ferrous ion/FZ complex is given in FIG. 4. As can be seen from FIG. 4, the color development is complete within 1-10 minutes and is remarkably stable for a period of at least 48 hours.

Using the above tests, boiler feed water ferrous ion pick-up studies were made across various boiler system units operating in a steel manufacturing plant. Samples

TABLE I

| Sample No | Fe(II), ppm Theoretical | Fe(III), ppm Theoretical | Fe (total), ppm Measured | Fe(II)/Fe(III) determination Fe(II), ppm Measured | Fe(III), ppm [Fe(tot) − Fe(II)] | Δ Fe(II) | % Error [Fe(II)] | Δ Fe(III) | % Error [Fe(III)] |
|---|---|---|---|---|---|---|---|---|---|
| 1 | 0.05 | 1.00 | 1.08 | 0.07 | 1.01 | 0.02 | 46 | 0.01 | 1 |
| 2 | 0.10 | 0.50 | 0.63 | 0.12 | 0.51 | 0.02 | 22 | 0.01 | 2 |
| 3 | 0.20 | 0.20 | 0.45 | 0.23 | 0.22 | 0.03 | 15 | 0.02 | 10 |
| 4 | 0.50 | 0.10 | 0.66 | 0.54 | 0.12 | 0.04 | 8 | 0.02 | 22 |
| 5 | 1.00 | 0.05 | 1.12 | 1.06 | 0.06 | 0.06 | 6 | 0.01 | 20 |

For each of the samples, the color development was completed within one minute, or earlier, at temperatures ranging from about 60° to about 80° F. The complex was stable to air oxidation for at least 48 hours. In spite of the oxygen stability for the ferrous/FZ complex, it is suggested that all measurements and sampling be made in an anaerobic environment. It is important that the sample to be analyzed from the boiler system unit be collected in a testing apparatus such that the sample is mixed with a solution of the FZ reagent in an anaerobic environment to prevent the iron in the system from reacting with other chemicals in the system.

Figure 2:
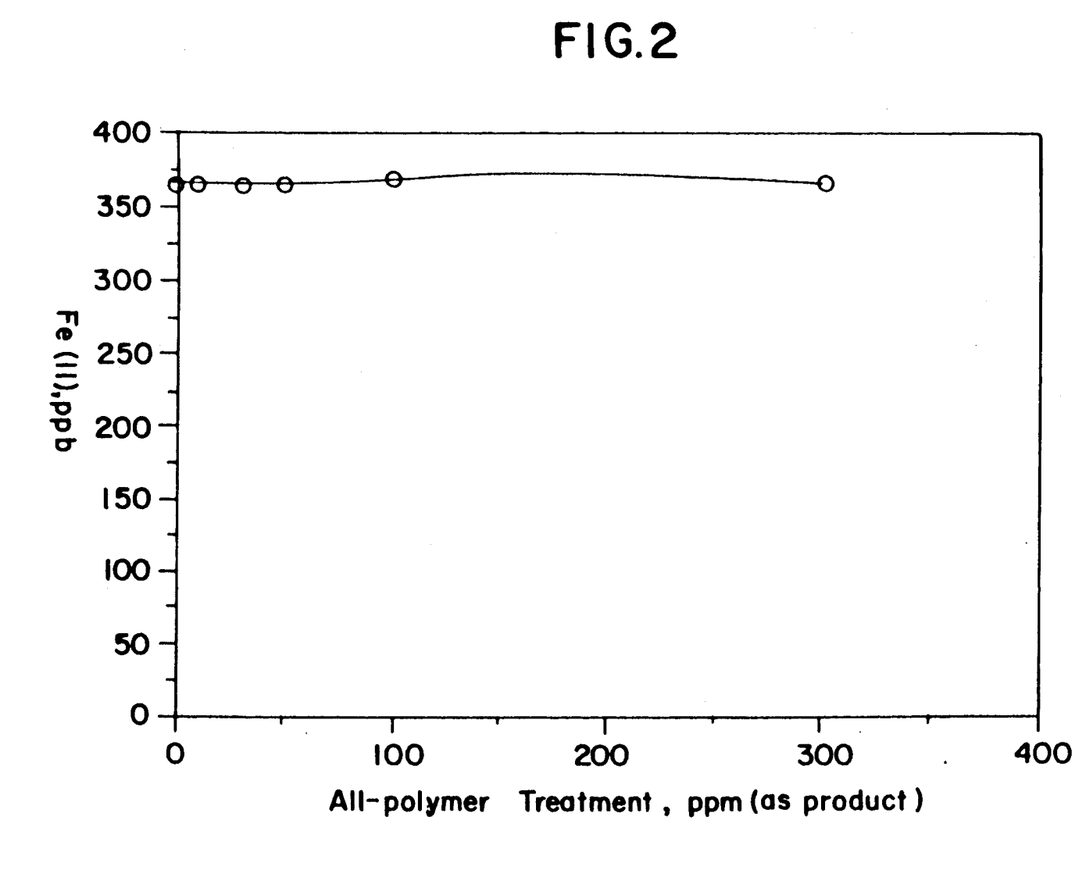
FIG. 2 is a graph showing the effect of all-polymer treatment concentrations on the formation of the ferrous ion/FZ complex.
Figure 3:
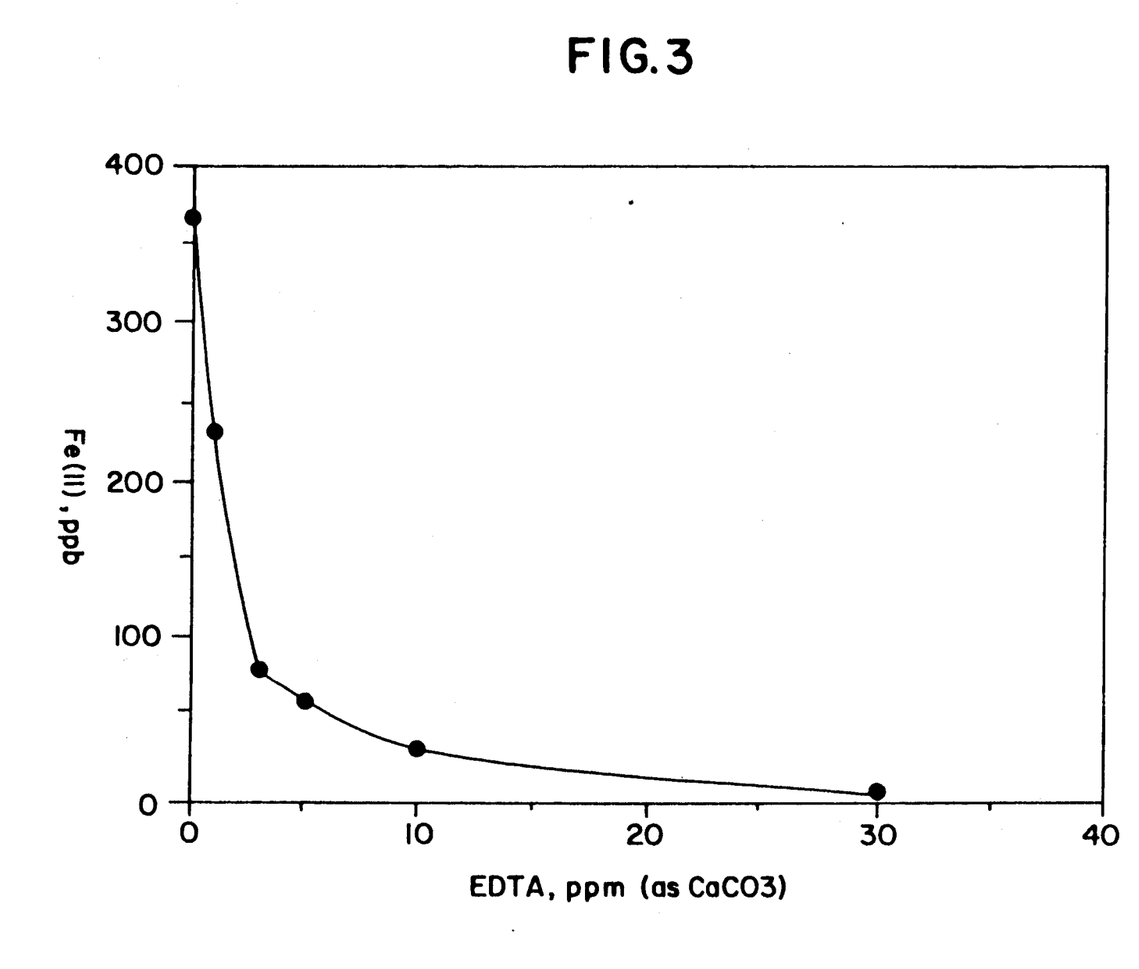
FIG. 3 is a graph showing the effect of EDTA concentrations on the formation of ferrous ion/FZ complex.

Prior to presenting the results of actual boiler unit tests, it was determined that ferrous ion in solution may be affected by the presence of certain internal boiler water chemical treatments. Towards this end, various water samples containing calculated amounts equaling 370 parts per billion ferrous ions, were spiked with these boiler water chemicals prior to admixture with the FZ reagent solution. A polymeric transport chemical provided by Nalco Chemical Company was spiked at a concentration up to 300 parts per million based on total product. Also, a solution of ethylene diamine tetraacetic acid, as partial sodium salt, was also spiked into the solution containing ferrous ions. FIGS. 2 and 3 provide the results of these tests.

In the presence of the polymeric transport chemical obtained from Nalco Chemical Company, and sold under the name Transport Plus ®[2], no negative effect was obtained for the determination of ferrous ion in solution. However, EDTA at a concentration equal to 1 part per million, calculated as calcium carbonate, affected ferrous ion determinations drastically. At an EDTA dosage of 30 ppm, as calcium carbonate, ferrous ion concentration detected by FZ reagent was below the detection limit.

[2]Transport Plus ® is a registered trademark of Nalco Chemical Company.

This interference can be eliminated by increasing the concentration of the FZ reagent as is shown in Table II, so that when the concentration of the FZ reagent is high enough compensation for the interference cause by the EDTA chelant is achieved.

Therefore, a key to monitoring for the presence of corrosion products, as measured by the presence of ferrous ion in boiler waters, particularly when those boiler waters are treated with certain boiler water treatment chemicals, is to have sufficient and effective concentrations of the FZ reagent present to overwhelm and across an economizer operating within this boiler were analyzed using the ferrous iron/FZ sampling and analysis procedures described above. Chemical treatment programs containing EDTA, as well as chemical treatment programs containing NTA and another chemical treatment programs containing an all-polymer transport treatment chemical were evaluated. Tests confirmed that corrosion across the economizer boiler unit was a direct function of the dosage of strong chelant chemical treating agents.

With no feed of boiler treatment chemical containing EDTA, or NTA, but with boiler treatment chemicals containing oxygen scavengers, such as carbohydrazide and erythorbic acid salts, the ferrous ion pickup levels were 0 parts per billion. When operating with boiler treatment chemicals used primarily for the purpose of transporting and controlling hardness scales and hardness scale creating chemicals such as magnesium, calcium, silicates and the like, ferrous ion determinations were directly increased as the dosage of the chemical chelant was increased. Ferrous ion levels were reported as high as 162 parts per billion when an EDTA containing formulation was added so as to retain 0.2 parts per million residual of the EDTA containing formulation. Ferrous ion levels were reported as high as 162 parts per billion when an EDTA containing formulation was added so as to retain 0.2 parts per million residual of the EDTA containing formulation. Ferrous ion levels were detected (with treatment at a 0.1 parts per million EDTA residual dosage) at concentrations ranging from 78-85 parts per billion with or without the presence of the above mentioned oxygen scavengers. Iron pickup levels using a program of boiler treatment chemicals presented as the Betz Company's B1986 program, which program led to dosages of a 0.1 ppm formula weight (B1986) residual, equalled 101 parts per billion ferrous ion, in the absence of either carbohydrazide or erythorbate. In the presence of a chemical treatment program in which the hardness complexing agent was nitrilotriacetic acid (NTA), ferrous ion was detected at 42 parts per billion when the NTA was added to the boiler system at a residual of 0.1 parts per million.

During the above tests, dissolved oxygen levels in the feed water were consistently controlled at 0 parts per billion.

Since corrosion is a direct function and is demonstrated directly by the presence of freshly generated ferrous ion, it is believed that Applicants' technique of monitoring boiler waters, particularly in the presence of boiler water treatment chemicals, using techniques which provide for adequate concentrations of FZ reagent so as to compensate and overwhelm any complexes formed by chelating agents present in the treating chemicals, such chelating agents demonstrated to include EDTA and NTA, is an accurate measure of actual corrosion.

Based on the results recited above, the formulations containing NTA were not nearly as aggressive in terms of creating corrosion of iron across the economizer as were the formulations containing EDTA.

In another series of tests, chemical treatment programs typically used to treat boiler waters, which programs contained EDTA and various polymers used as dispersants also were demonstrated to show iron pickup in these boiler samples in the form of ferrous ion which could be monitored using the ferrous ion/FZ proportional monitoring techniques of this invention. Corrosion potential, as measured by the concentrations of ferrous ion determined in the boiler system waters, appeared to increase directly as the concentration of the EDTA increased. Earlier tests using polymers indicated that the polymers had no essential effect under these test conditions.

Table III presents the results obtained when an operating economizer was monitored using the techniques of Applicants' invention for iron pickup.

TABLE III

Economizer Iron Pickup Study

| Chelant | FW Chelant Dosage (ppm) as CaCO3 | FW Chelant Residual (ppm) as CaCO3 | Economizer ΔFe(II) ppb | Economizer ΔFe (Total) ppb |
|---|---|---|---|---|
| EDTA | 0.35 | 0.30 | 152 | 159 |
| EDTA | 0.14 | 0.09 | 85 | 85 |
| EDTA | 0.14 | 0.09 | 78 | 84 |
| EDTA | 0.35 | 0.30 | 120 | 136 |
| EDTA | 0.30 | 0.25 | 151 | 138 |
| none | 0.00 | 0.00 | 0 | 4 |
| NTA | 0.30 | 0.25 | 96 | 93 |
| NTA | 0.15 | 0.10 | 42 | 43 |
| EDTA | 0.25 | 0.20 | 128 | 125 |
| none | 0.00 | 0.00 | · 1 | — |
| EDTA | 0.24 | 0.00 | 85 | — |
| EDTA | 0.24 | 0.16 | 133 | — |
| EDTA | 0.24 | 0.19 | 156 | 163 |
| EDTA | 0.24 | 0.19 | 162 | — |
| EDTA | 0.24 | 0.19 | 149 | — |
| EDTA | 0.07 | 0.02 | 48 | 48 |
| EDTA | 0.15 | 0.10 | 101 | 102 |

1. ΔFe(II) or ΔFe(Total) = Fe(II) or (Total) at the economizer outlet — (minus) Fe(II) or (Total) at the economizer inlet
2. $Fe_{(Total)} = Fe_{II} + Fe_{(III)}$ As can be observed, the data in Table III also presents the total iron found in the economizer boiler samples. This total iron was remarkably close to the ferrous ion in practically all cases and demonstrates that the iron presence in the economizer boiler waters was not present because of contaminations, scaling or residual iron but in fact was present almost exclusively from the formation of ferrous ion in a corrosive mechanism.

Further tests were completed on line at various treatment levels for each of the EDTA containing, NTA containing, or all-polymer treatment programs normally found in the industry. Table IV presents the data obtained when this boiler system was operated with the listed percentages of recommended dosages for various formulations which contained, as the primary hardness treatment reagents, EDTA, NTA, or all-polymer treatment formulations. The data for EDTA, #1, was obtained from a treatment program suggested by one water treatment chemical company, EDTA #2, was from a treatment program suggested by that same company but having a slightly different formulation, EDTA, #3 was obtained from a second water treatment chemical company and the NTA and all polymer programs were also commercially available products.

TABLE IV

Economizer Iron Pickup Study

| % Recommended Dosage For Hardness Control* | Fe-II Economizer Pickup |
|---|---|
| EDTA #1 | |
| 100% | 152 |
| 30 | 85 |
| 30 | 78 |
| 100 | 120 |
| 83 | 151 |
| EDTA #2 | |
| 53 | 133 |
| 63 | 156 |
| 63 | 162 |
| 63 | 149 |
| EDTA #1 | 30 |
| 8 | 45 |
| BASELINE (with Erythorbate Oxygen Scavenger) | |
| 0 | 0 |
| 0 | 1 |
| EDTA #3 | |
| 7 | 48 |
| 33 | 101 |
| NTA | 96 |
| 83 | |
| 33 | 42 |
| ALL-POLYMER | |
| 100 | 2 |
| 200 | 2 |

Figure 5:
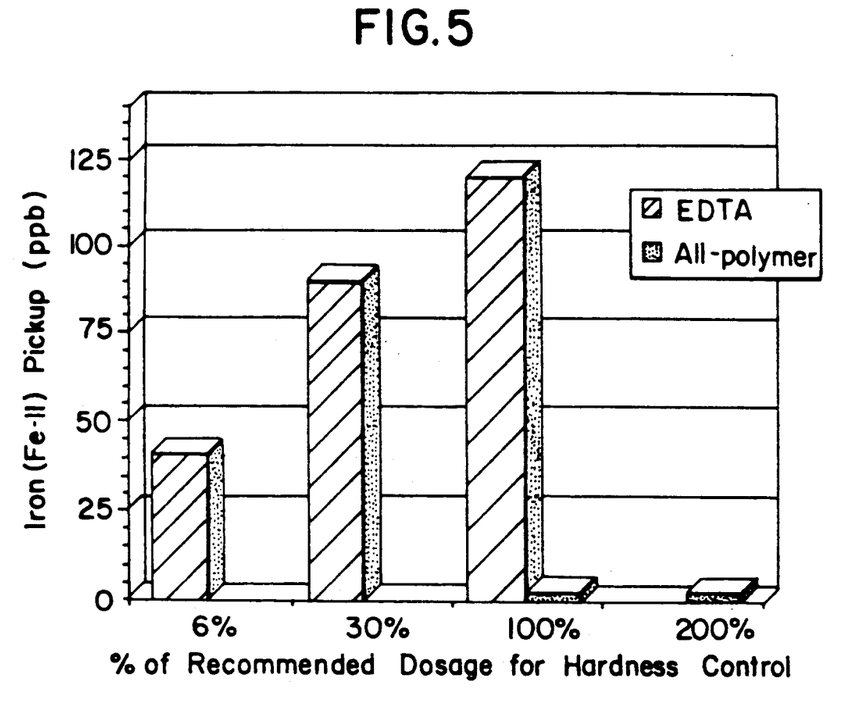
FIG. 5 is a graph showing iron pick up, as measured by ferrous ion/FZ complexation, when an EDTA based treatment program is compared to an all-polymer treatment program for scale control.

FIG. 5 presents the iron pickup, as measured by ferrous ion/FZ complexation, when an EDTA based treatment program is compared to an all polymer treatment program for scale control. The recommended dosages for hardness control using EDTA are averages of treatment systems recommended by two separate boiler treatment chemical companies. By measuring ferrous ion according to the techniques described and claimed herein, it is clear that the all polymer program can provide both corrosion free environments and hardness scale transport and hardness scale minimization.

Having described our invention, we claim:

1. A method of determining actual corrosion rates of boiler system ferrometals in contact with boiler system waters containing boiler water treatment chemicals, which method comprises the steps of:

obtaining a known aliquot volume of a boiler water sample;

adding the known volume of the sample to a known volume of an acetate solution, buffered at pH from 2.0 to 6.0, the acetate solution including an effective concentration of 3-(2-pyridyl)-5,6-diphenyl-1,2,4-triazine-p,p'-disulfonic acid monosodium salt monohydrate reagent, wherein no reducing agents are added prior to the step of adding the known volume of sample to the known volume of the buffered acetate solution;

mixing the sample and acetate solution to form a soluble ferrous ion/3-(2-pyridyl)-5,6-diphenyl-1,2,4-triazine-p,p'-disulfonic acid complex solution;

generating a standard ferrous ion/3-(2-pyridyl)-5,6-diphenyl-1,2,4-triazine-p,p'-disulfonic acid absorbance curve for a standard solution containing a known value of 3-(2-pyridyl)-5,6-diphenyl-1,2,4-triazine-p,p'-disulfonic acid;

measuring spectrophotometrically the absorbance of the ferrous ion/3-(2-pyridyl)-5,6-diphenyl-1,2,4-triazine-p,p'-disulfonic acid complex solution at a wavelength of about 560±30 nanometers;

calculating the amount of ferrous ion present by comparing the absorbance of the ferrous ion/3-(2-pyridyl)-5,6-diphenyl-1,2,4-triazine-p,p'-disulfonic complex solution acid to the standard absorbance curve;

repeating the steps of obtaining, adding, mixing, generating, measuring and calculating so as to determine an actual corrosion rate.

2. The method of claim 1 wherein the standard solution of 3-(2-pyridyl)-5,6-diphenyl-1,2,4-triazine-p,p'-disulfonic acid reagent contains an effective amount of the reagent to form the ferrous ion/3-(2-pyridyl)-5,6-diphenyl-1,2,4-triazine-p,p'-disulfonic acid complex in essentially quantitative amounts.

3. The method of claim 2 wherein the steps of obtaining said boiler water sample, adding said boiler water sample to the 3-(2-pyridyl)-5,6-diphenyl-1,2,4-triazine-p,p'-disulfonic acid reagent, measuring the absorbance of ferrous ion/3-(2-pyridyl)-5,6-diphenyl-1,2,4-triazine-p,p'-disulfonic acid complex and comparing the absorbance to said standard curve are performed in an anerobic environment.

4. The method of claim 2 wherein the boiler water sample is taken from boiler system units selected from the group consisting of inlets and outlets of an economizer, a pre-heater, a condensate system, any holding tank or vessel, a turbine, any piston driven device, a water wall header, boiler inlet lines, boiler blowdown lines, a deaerator, or any combination thereof.

5. The method of claim 2 wherein the boiler water sample is taken from boiler system units selected from the group consisting of inlets and outlets of steam condensors, boiler feedwater, boiler blowdown, storage vessels, holding tanks, receivers, heat exchangers, turbines, pistons, and water wall headers.

6. The method of claim 5 wherein the steps of obtaining said boiler water sample, adding said boiler water sample to the 3-(2-pyridyl)-5,6-diphenyl-1,2,4-triazine-p,p'-disulfonic acid reagent, measuring the absorbance of ferrous ion/3-(2-pyridyl)-5,6-diphenyl-1,2,4-triazine-p,p'-disulfonic acid complex and comparing the absorbance to said standard curve are performed automatically and continuously.

7. The method of claim 5 wherein the standard 3-(2-pyridyl)-5,6-diphenyl-1,2,4-triazine-p,p'-disulfonic acid reagent solution has a pH of from 3.4 to about 3.8 and contains at least 0.005 moles per liter of 3-(2-pyridyl)-5,6-diphenyl-1,2,4-triazine-p,p'-disulfonic acid.

8. The method of claim 5 comprising the additional steps of:

adding a known amount of a strong reducing agent chosen from the group consisting of hydroxylamine hydrochloride, thioglycolic acid or its salts, erythorbic acid or its salts, hydrazine, carbohydrazide, sodium bisulfite and mixtures thereof to the ferrous ion/3-(2-pyridyl)-5,6-diphenyl-1,2,4-triazine-p,p'-disulfonic acid complex solution;

mixing and reacting the reducing agent and complex solution for a sufficient time to reduce any ferric ion species present to ferrous ion, which ferrous ion reacts with residual 3-(2-pyridyl)-5,6-diphenyl-1,2,4-triazine-p,p'-disulfonic acid reagent, forming additional ferrous ion/3-(2-pyridyl)-5,6-diphenyl-1,2,4-triazine-p,p'-disulfonic acid complexes in the mixed and reacted solution;

remeasuring the absorbance of the mixed and reacted solution; and calculating total iron content by subtracting the original ferrous ion content from total iron content after the step of remeasuring.

9. The method of claim 8, wherein the strong reducing agent is thioglycolic acid.

* * * * *